US006942778B1

(12) United States Patent
Jalali et al.

(10) Patent No.: US 6,942,778 B1
(45) Date of Patent: Sep. 13, 2005

(54) MICROSTRUCTURE APPARATUS AND METHOD FOR SEPARATING DIFFERENTLY CHARGED MOLECULES USING AN APPLIED ELECTRIC FIELD

(75) Inventors: Shila Jalali, San Diego, CA (US); Alan Harper, Jamul, CA (US); Matt Simpson, San Diego, CA (US); Paul Swanson, Santee, CA (US); John Havens, San Diego, CA (US)

(73) Assignee: Nanogen, Inc., San Diego, CA (US)

( * ) Notice: Subject to any disclaimer, the term of this patent is extended or adjusted under 35 U.S.C. 154(b) by 423 days.

(21) Appl. No.: 09/724,909

(22) Filed: Nov. 28, 2000

(51) Int. Cl.$^7$ ............................................. G01N 27/453
(52) U.S. Cl. ..................... 204/605; 204/601; 204/603
(58) Field of Search .............................. 204/600, 601, 204/605, 606, 614, 627

(56) References Cited

U.S. PATENT DOCUMENTS

| | | | |
|---|---|---|---|
| 5,376,252 A | 12/1994 | Ekstrom | 204/299 R |
| 5,580,747 A | 12/1996 | Shultz | 435/24 |
| 5,858,188 A | 1/1999 | Soane | 204/454 |
| 5,904,824 A | 5/1999 | Oh | 204/601 |
| 5,932,315 A | 8/1999 | Lum | 428/172 |
| 5,942,443 A | 8/1999 | Parce | 436/514 |
| 5,948,227 A | 9/1999 | Dubrow | 204/455 |
| 5,957,579 A | 9/1999 | Kopf-Sill | 366/340 |
| 5,958,202 A | 9/1999 | Regnier | 204/451 |
| RE36,350 E * | 10/1999 | Swedberg et al. | 210/198.2 |
| 5,965,001 A | 10/1999 | Chow | 204/600 |
| 5,976,336 A | 11/1999 | Dubrow | 204/453 |
| 6,001,229 A * | 12/1999 | Ramsey | 204/451 |
| 6,046,056 A | 4/2000 | Parce | 436/514 |
| 6,056,859 A * | 5/2000 | Ramsey et al. | 204/451 |
| 6,068,752 A | 5/2000 | Dubrow | 204/604 |
| 6,074,827 A | 6/2000 | Nelson | 435/6 |
| 6,093,296 A | 7/2000 | Soane | 204/451 |
| 6,103,199 A * | 8/2000 | Bjornson et al. | 422/100 |
| 6,103,537 A * | 8/2000 | Ullman et al. | 436/526 |
| 6,167,910 B1 * | 1/2001 | Chow | 137/827 |
| 6,623,860 B2 * | 9/2003 | Hu et al. | 428/411.1 |

FOREIGN PATENT DOCUMENTS

| | | | | |
|---|---|---|---|---|
| JP | 62-247247 | 10/1987 | | |
| JP | 11311616 A | * 11/1999 | | G01N 27/447 |
| WO | 98/10277 | 3/1998 | | |
| WO | WO98/45693 | 10/1998 | | |
| WO | WO99/15876 | 4/1999 | | |
| WO | WO99/15888 | 4/1999 | | |

(Continued)

OTHER PUBLICATIONS

Folch et al., "Molding of Deep Polydimethylsiloxane Microstructures for Microfluidics and Biological Applications", *Journal of Biomechanical Engineering*, 121: 28-34 (1999).

(Continued)

*Primary Examiner*—Alex Noguerola
(74) *Attorney, Agent, or Firm*—Morgan, Lewis & Bockius LLP

(57) ABSTRACT

The field of the present invention relates generally to a microstructure apparatus which may be used in a high-throughput screening context to monitor the rate of reaction of an enzyme with its substrate in cases where the product of the reaction has an altered net charge. For example, the systems and methods disclosed herein may be used to detect the activity of phosphatase enzymes, proteases and kinases on charged peptide substrates. The microstructure devices of the present invention comprise a plurality of microstructures, wherein each microstructure comprises a capture matrix located between two electrodes.

50 Claims, 11 Drawing Sheets

FOREIGN PATENT DOCUMENTS

| WO | WO99/19717 | 4/1999 |
|----|------------|--------|
| WO | WO99/40174 | 8/1999 |
| WO | WO00/50871 | 8/2000 |

OTHER PUBLICATIONS

Ford et al., "Micromachining in Plastics Using X-Ray Lithography for the Fabrication of Micro-Electrophoresis Devices", *Journal of Biomechanical Engineering*, 121: 13-21 (1999).

Jackman et al., "Design and Fabrication of Topologically Complex, Three-Dimensional Microstructures", *Science*, 280: 2089-2091 (1998).

Martin et al., "Dual-Electrode Electrochemical Detection for Poly(dimethylsiloxane)-Fabricated Capillary Electrophoresis Microchips", *Analytical Chemistry*, 72: 3196-3202 (2000).

Pang et al., "DNA Sequencing Using 96-Capillary Array Electrophoresis", *Journal of Biochemical and Biophysical Methods*, 41: 121-132 (1999).

Shi et al., "Radial Capillary Array Electrophoresis Microplate and Scanner for High-Performance Nucleic Acid Analysis", *Analytical Chemistry*, 71: 5354-5361 (1999).

Simpson et al., "High-throughput Genetic Analysis Using Microfabricated 96-Sample Capillary Array Electrophoresis Microplates", *Proc. Natl. Acad. Sci. USA*, 95: 2256-2261 (1998).

Wu et al., "Analysis of Src Kinase and Protein Kinase C Activity by Capillary Electrophoresis and Laser-Induced Fluorescence", *Analytical Biochemistry*, 269: 423-425 (1999).

Anderson et al., Fabrication of Topologically Complex Three-Dimensional Microfluidic Systems in PDMS by Rapid Prototyping, *Analytical Chemistry*, 72: 3158-3164 (2000).

Cohen et al., "A Microchip-Based Enzyme Assay for Protein Kinase A", *Analytical Biochemistry*, 273: 89-97 (1999).

Deng et al., "Prototyping of Masks, Masters, and Stamps/Molds for Soft Lithography Using an Office Printer and Photographic Reduction", *Analytical Chemistry*, 72: 3176-3180 (2000).

Duffy et al., "Rapid Prototyping of Microfluidic Systems in Poly(dimethylsiloxane)", *Analytical Chemistry*, 70: 4974-4984 (1998).

* cited by examiner

MICROSTRUCTURE APPARATUS AND METHOD FOR SEPARATING DIFFERENTLY CHARGED MOLECULES USING AN APPLIED ELECTRIC FIELD

FIELD OF INVENTION

The field of the present invention relates generally to a microstructure apparatus which may be used in a high-throughput screening context to monitor the rate of reaction of an enzyme with its substrate in cases where the product of the reaction has an altered net charge. For example, the systems and methods disclosed herein may be used to detect the activity of phosphatase enzymes, proteases and kinases on charged peptide substrates. The microstructure devices of the present invention comprise a plurality of microstructures, wherein each microstructure comprises a capture matrix located between two electrodes.

BACKGROUND OF THE INVENTION

Protein kinases are of particular interest in drug discovery research because they have been shown to be key regulators of many cell functions, including signal transduction (Ullrich and Schlessinger, 1990), transcriptional regulation (Pawson and Bernstein, 1990), cell motility (Miglietta and Nelson, 1988) and cell division (Pines and Hunter, 1990). Protein kinases are enzymes which covalently modify proteins and peptides by the attachment of a phosphate group to one or more sites on the protein. Phosphatases perform the opposite function. Many of the known protein kinases use adenosine triphosphate (ATP) as the phosphate donor, placing the γ-phosphate onto a histidine, tyrosine, serine or threonine residue in the protein. The location of the modification site and the type of residue modified by the kinase are usually specific for each particular kinase.

The added phosphate alters certain structural, thermodynamic and kinetic properties of the phosphorylated protein. Generally, the phosphate adds two negative charges to the protein. This modifies the electrostatic interactions between the protein's constituent amino acids, in turn altering secondary and tertiary protein structure. The phosphate may also form up to three hydrogen bonds or salt bridges with other protein residues, or may otherwise change the conformational equilibrium between different functional states of the protein. These structural changes provide the basis, in a biological system, for altering substrate binding and catalytic activity of the phosphorylated proteins.

Phosphorylation and dephosphorylation reactions, under the control of kinases and phosphatases, respectively, can occur rapidly to form stable structures. This makes the phosphorylation system ideal as a regulatory process. Phosphorylation and dephosphorylation reactions may also be part of a cascade of reactions that can amplify a signal that has an extracellular origin, such as hormones and growth factors.

Methods for assaying the activity of protein kinases often utilize a synthetic peptide substrate that can be phosphorylated by the kinase protein under study. The most common mechanisms for detecting phosphorylation of the peptide substrates are 1) Incorporation of $^{32}P$ (or $^{33}P$) phosphate from $[^{32}P]\gamma$-ATP into the peptides, purification of the peptides from ATP, and scintillation or Cherenkov counting of the incorporated radionucleotide, 2) Detection of phospho-amino acids with radiolabeled specific antibodies, or 3) Purification of phosphorylated peptides from unphosphorylated peptides by chromatographic or electrophoretic methods, followed by quantification of the purified product.

For example, in one widely used method, a sample containing the kinase of interest is incubated with activators and a substrate in the presence of gamma $^{32}P$-ATP, with an inexpensive substrate, such as histone or casein being used. After a suitable incubation period, the reaction is stopped and an aliquot of the reaction mixture is placed directly onto a filter that binds the substrate. The filter is then washed several times to remove excess radioactivity, and the amount of radiolabelled phosphate incorporated into the substrate is measured by scintillation counting (Roskoski, 1983).

The use of $^{32}P$ in assays, however, poses significant disadvantages. One major problem is that, for sensitive detection, relatively high quantities of $^{32}P$ must be used routinely and subsequently disposed. The amount of liquid generated from the washings is not small, and contains $^{32}P$. Due to government restrictions, this waste cannot be disposed of easily. It must be allowed to decay, usually for at least six months, before disposal. Another disadvantage is the hazard posed to personnel working with the isotope. Shielding and special waste containers are inconvenient but necessary for safe handling of the isotope. Further, the lower detection limit of the assay is determined by the level of background phosphorylation and is therefore variable. In short, the study of protein kinases would be greatly facilitated by the development of an efficient and accurate assay that does not require the use of radioactivity.

Although radioisotope methods have been applied in high throughput screening, the high cost and strict safety regulation incurred with the use of radioisotopes in high throughput screening greatly limits their use in drug discovery. For these and other reasons, it would be useful to develop alternative methods and apparatus for high throughput screening that facilitate measuring the kinase dependent phosphorylation of peptides.

Recently, several analytical chemistry research groups have experimented with micro-lithographed electrophoretic separation devices. These devices typically contain four or more reservoirs connected by a cross-shaped arrangement of channels. A long, sinuous channel is usually situated at the tail of the cross, which is utilized for electrophoretic separation of charged molecules in the system. These devices rely on electro osmotic flow (EOF) forces to provide flow of the solution through the system, and thus all molecules (positive, negative, and uncharged) in the sample are transported in the same direction along the separation channel, their speed and position determined by their net charge/mass. In order to detect each molecule in the sample, a continuous detection system is used during the electrophoretic separation process. Because of their reliance on EOF forces, these devices must be manufactured to high tolerance (with small cross-section microchannels) and are designed to include a rather long separation path.

SUMMARY OF THE INVENTION

The devices and methods of the present invention provide a simple solution to the problem of separating differently charged molecules in a sample for the detection of a molecule of interest. These methods and devices are particularly suitable for analyzing substrate-enzyme reactions, or other simple biochemical model systems where a labeled molecule may undergo change in net charge, in a highly parallel manner. The devices of the invention utilize a capture matrix located in the electrophoretic path of the charged molecule of interest in order to capture that molecule for later analysis.

Thus, continuous detection of molecules traveling along the electrophoretic path is not necessary with the devices of the present invention. Moreover, because they do not utilize migration speed in solution in order to separate the charged molecules, the devices of the invention are able to use much shorter and direct migration paths, simplifying device design and construction.

Thus, in one aspect, the current invention provides novel systems for separating peptides, or other molecules in a sample having different net charges, for detection and quantification.

In preferred embodiments of this aspect of the invention, the one or more samples are simultaneously assayed in the system, which contains one or more microstructures to separate the charged molecules in the sample. Each microstructure comprises a capture matrix, which, after the individual samples containing molecules of different charges are introduced into the microstructures, electrophoresed, and concentrated in the capture matrix section of the microstructure, binds or holds the molecules of interest for detection. The systems of the invention comprise:
 a) a microstructure plate comprising:
  at least one microstructure, each microstructure comprising a series of microstructure sections and channels, wherein each microstructure section is directly interconnected to at least one other microstructure section by at least one channel, the series comprising:
   at least one sample accepting microstructure section, wherein the sample accepting section is fluidly connected to the exterior of the microstructure plate;
   at least one first electrode microstructure section;
   at least one second electrode microstructure section;
   at least one capture microstructure section containing a capture matrix, wherein the capture microstructure section is between the first and second electrode microstructure sections in the series;
  wherein the microstructures in the microstructure plate are formed by at least two layers of material, wherein at least one layer is a sealing plate layer which seals at least one channel or microstructure section in the assembled microstructure plate; and
 b) an electrode assembly, the electrode assembly having at least one first and at least one second electrode, wherein each first electrode microstructure section is in electrical contact with at least one first electrode, and wherein each second electrode microstructure section is in electrical contact with at least one second electrode.

Preferred embodiments of the system comprise a plurality of microstructure units, preferably arrayed in a rectangular fashion. These systems may be compatible with 96, 384, or 1536 well microtiter plate formats, and compatible with microtiter plate loaders and readers, such as absorbance or fluorescence microtiter plate readers. This allows for the simultaneous processing of a plurality of samples for high-throughput screening applications by simultaneously loading the samples into the system and simultaneously subjecting the samples to electrophoresis.

The microstructure plate contains at least one opening to the exterior of the plate for the introduction of the sample into the microstructure unit(s) of the plate. This opening may be in either the sealing plate, or in other layers of the microstructure plate. In other embodiments, other openings to the exterior may be present in the microstructure plate to allow access by electrodes, or for optical access to the capture matrix for detection of the charged molecule of interest. In preferred embodiments of the invention, at least one layer of the microstructure plate is optically transparent, which allows optical access to the capture matrix without an opening.

The geometry of the microstructure may be planar or three dimensional, as illustrated by the exemplary embodiments below. As illustrated, N or V shaped microstructure devices are exemplary useful geometries, but linear and sinuous embodiments would also be suitable for use in the systems of invention. One, two, or more capture matrices may be used to capture one or both of positively and negatively charged molecules separated in various embodiments of the system. The electrode assembly may be held in a separate plate support for use with the microstructure plate, or may be integrated into one or more layers of the microstructure plate. In exemplary embodiments of the system, the electrode assembly is an arrayed set of paired first and second pin electrodes held on a rigid plate, which may be brought into contact with the first and second electrode sections of the microstructures through openings in the microstructure plate.

In another aspect of the invention, methods are provided for using the systems of the invention to separate a charged molecule of interest from a sample mixture of molecules, and detect the amount of the charged molecule of interest in the sample. The system may be used to detect the activity of kinase, protease, or phosphatase enzymes on peptide substrates, and may generally be applied to monitor the chemical modification of a molecule resulting in a product of altered net charge. Generally, the method comprises the steps of:
 a) filling the microstructure with a liquid,
 b) introducing a sample into a sample accepting microstructure section of the apparatus,
 c) energizing the electrode assembly for a sufficient period of time to allow a charged molecule of interest in the sample to migrate towards an electrode of the electrode assembly and to be caught in the capture matrix, and
 d) detecting the charged molecule of interest caught in the capture matrix.

In preferred embodiments of the methods of the invention, an aqueous buffer is utilized as the liquid in the device. Optionally, the method may also include device assembly steps, such as the placement of the capture matrix within the microstructure plate, or aligning the electrode assembly with the microstructure plate and bringing it into electrical contact with the first and second electrode sections of the microstructures. Any suitable means for detection may be used in the methods of the invention, including consisting fluorometry, colorimetry, luminometry, mass spectrometry, electrochemical detection, and radioactivity detection. Fluorometry is preferred for use in the present invention, because of the ease handling fluorophores, and the commercial availability of fluorescent microtiter plate readers.

DEFINITIONS

As used herein, "microstructure" generally refers to structures which are fabricated on the scale of about 2 cm or less. The microstructures utilized in the present invention comprise a series of branched or unbranched channels connection a plurality of sections. A "microstructure section" (e.g., a constriction containing the capture matrix), may be larger than, smaller than or the same size as the channels. In embodiments of the systems of the invention where all of the microstructure sections are the same size as the channels, then the microstructure will comprise a continuous branched or unbranched channel with sections defined by function (first and second electrode, capture, and sample-accepting sections). Thus, although the circular chamber structure is a preferred embodiment of the systems of the invention, other embodiments of the systems are not limited to a strict chamber-channel series structure.

DETAILED DESCRIPTION OF THE INVENTION

The system and methods as described herein permit simultaneous electrophoretic separation of peptides, and other molecules having different net charges, in a parallel fashion for a large number of samples. The systems and methods of the invention are easily adapted for use with a variety of loading and detection equipment, including commercial sample loaders and microtiter plate readers, allowing for smooth integration of the systems with other equipment utilized in combinatorial synthesis and high-throughput drug discovery screening. Additionally, because the systems and methods of the invention provide a "snapshot" analytical view, rather than a dynamic, time-dependent view of the molecular species of interest, the electrophoretic separation and detection steps may be performed separately, greatly reducing the complexity and expense of the detection systems required for use in the methods of the invention.

General Microstructure Unit Design Considerations

Figure 1:
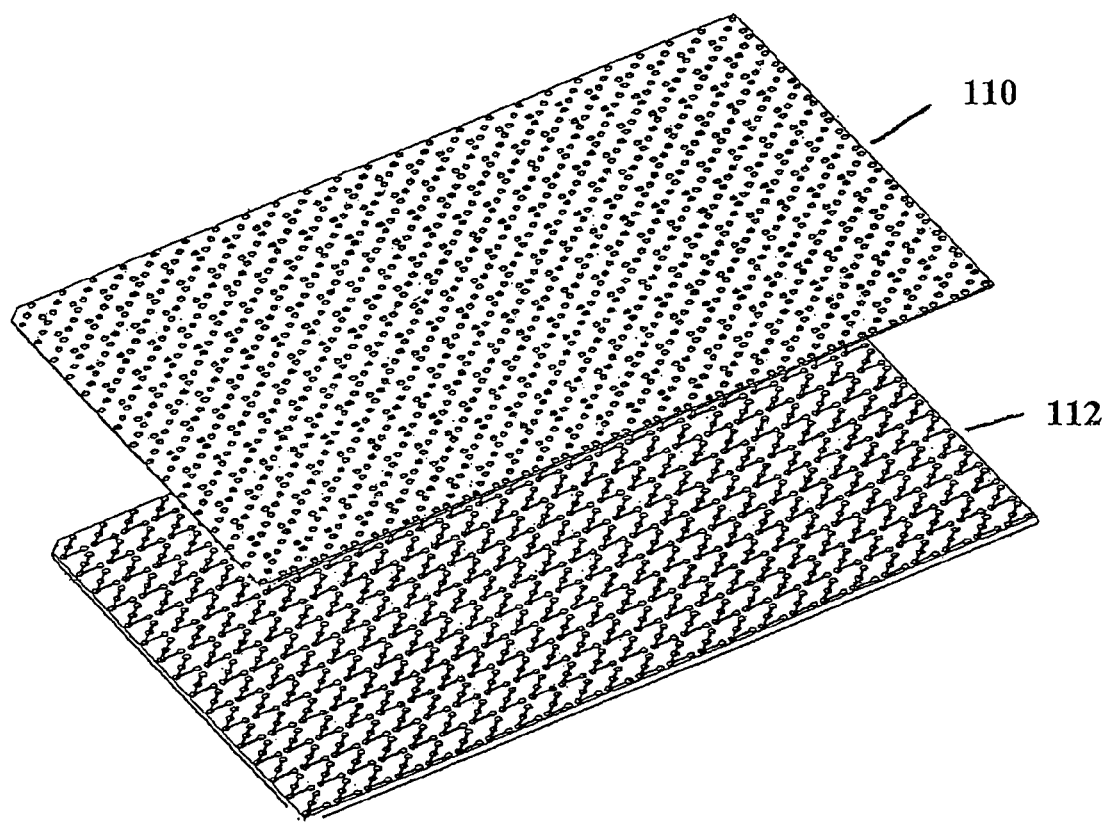
FIG. 1: A schematic for the first layer (110) and second layer (112) of a 384 unit "one capture" format device.
Figure 4A:
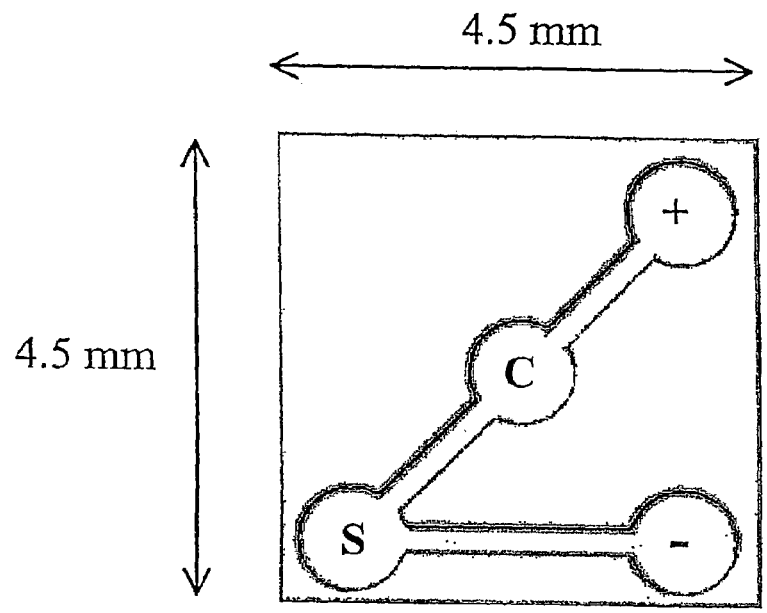
FIG. 4a: A schematic of a "one-capture" microstructure unit of an embodiment of the invention, as seen from above. (+) and (−) designate the electrode ports, which contain the electrodes in the assembled device. The (S) designates the sample port, which has an opening for the introduction of a sample into the micro structure. (C) designates the capture microstructure section, which contains the capture matrix.

The systems of the present invention generally comprise two main components: a microstructure plate containing one or more separatory microstructure units, and an electrode assembly. Although single-unit devices are within the scope of the invention, devices with a plurality of microstructure units are preferred because of the parallel sample processing advantages that they offer. As shown in FIG. 1, the microstructure units may be easily assembled into rectangular arrays which are compatible with standard 96, 384, or 1536 well microtiter plate formats, in order to facilitate use with automated loaders or microtiter plate readers. The microstructure shown in FIGS. 4a and 4b was used to construct an array of 384 microstructures in an 8.5X11 cm microstructure plate.

The microstructure plate is a laminar structure which forms the set of microstructures. Each microstructure comprises a set of microstructure sections (defined by function) and channels connecting those sections. The microstructures include at least one sample accepting microstructure section, which is fluidly connected to the exterior of the microstructure plate. Usually this fluid connection is accomplished by an opening in one or more layers of the microstructure plate. The microstructures also include at least one first electrode microstructure section and at least one second electrode microstructure section. These sections are either adapted to accept an electrode (e.g., have openings to the exterior of the microstructure plate which permit the entry of pin electrodes), or contain electrodes (e.g., integrally molded electrodes). Finally, the microstructures include at least one capture microstructure section containing a capture matrix. This capture microstructure section, which is between the first and second electrode microstructure sections in the series, binds or holds the charged molecule of interest when a sample is electrophoresed, so that the molecule may later be detected. Openings to the exterior of the microstructure plate for the injection of samples, access of electrodes, or for optical access to the capture chamber, may be present in various embodiments of the system. These openings may be formed in any layer of the microstructure plate, including the sealing plate layer described below.

Figure 2:
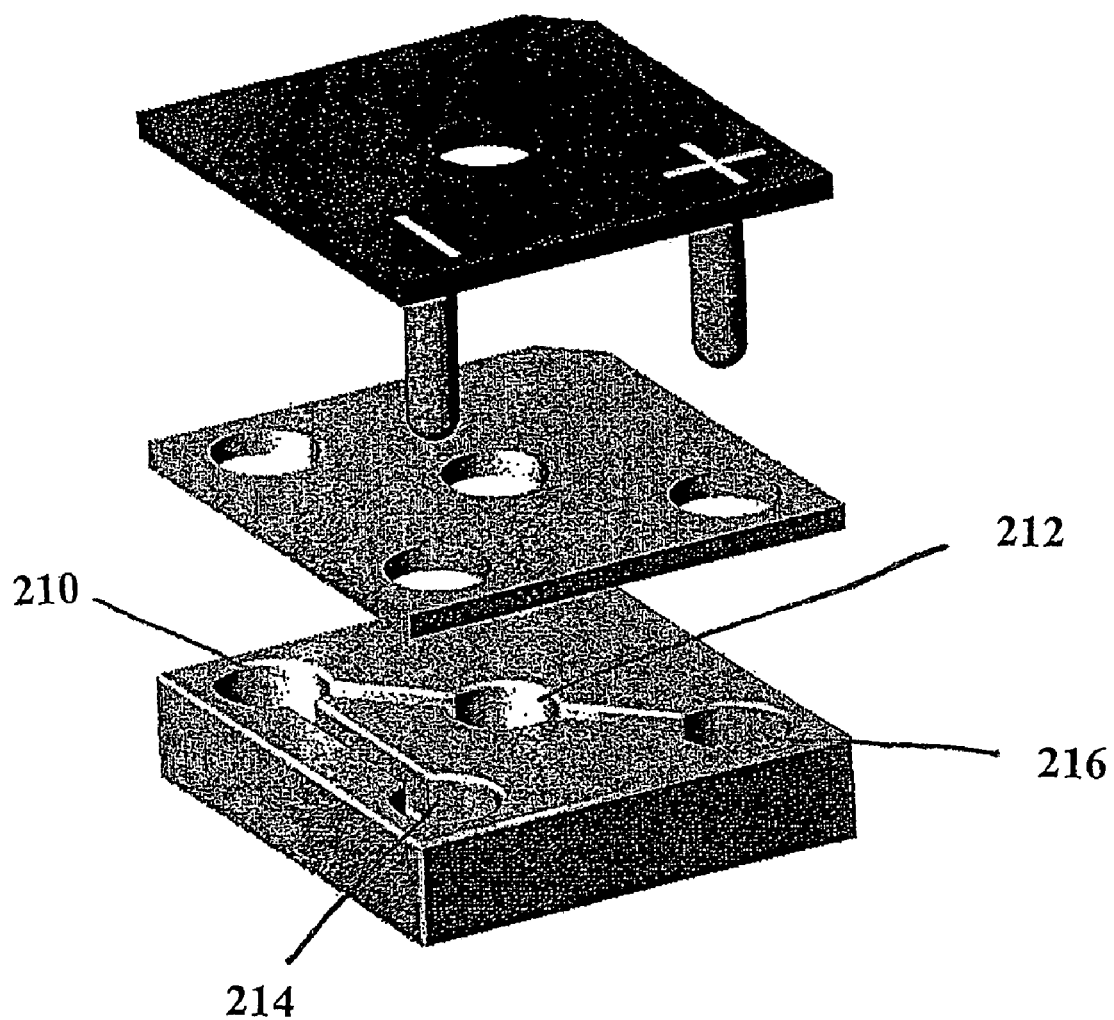
FIG. 2: A schematic for a "one-capture" format unit of the microstructure plate with electrode assembly with the sample accepting microstructure section, or chamber (210) at the point of the V, the first electrode (214) and second electrode (216) microstructure sections at the two tips of the V, and the capture microstructure section (212) between the accepting chamber and the electrode.
Figure 3:
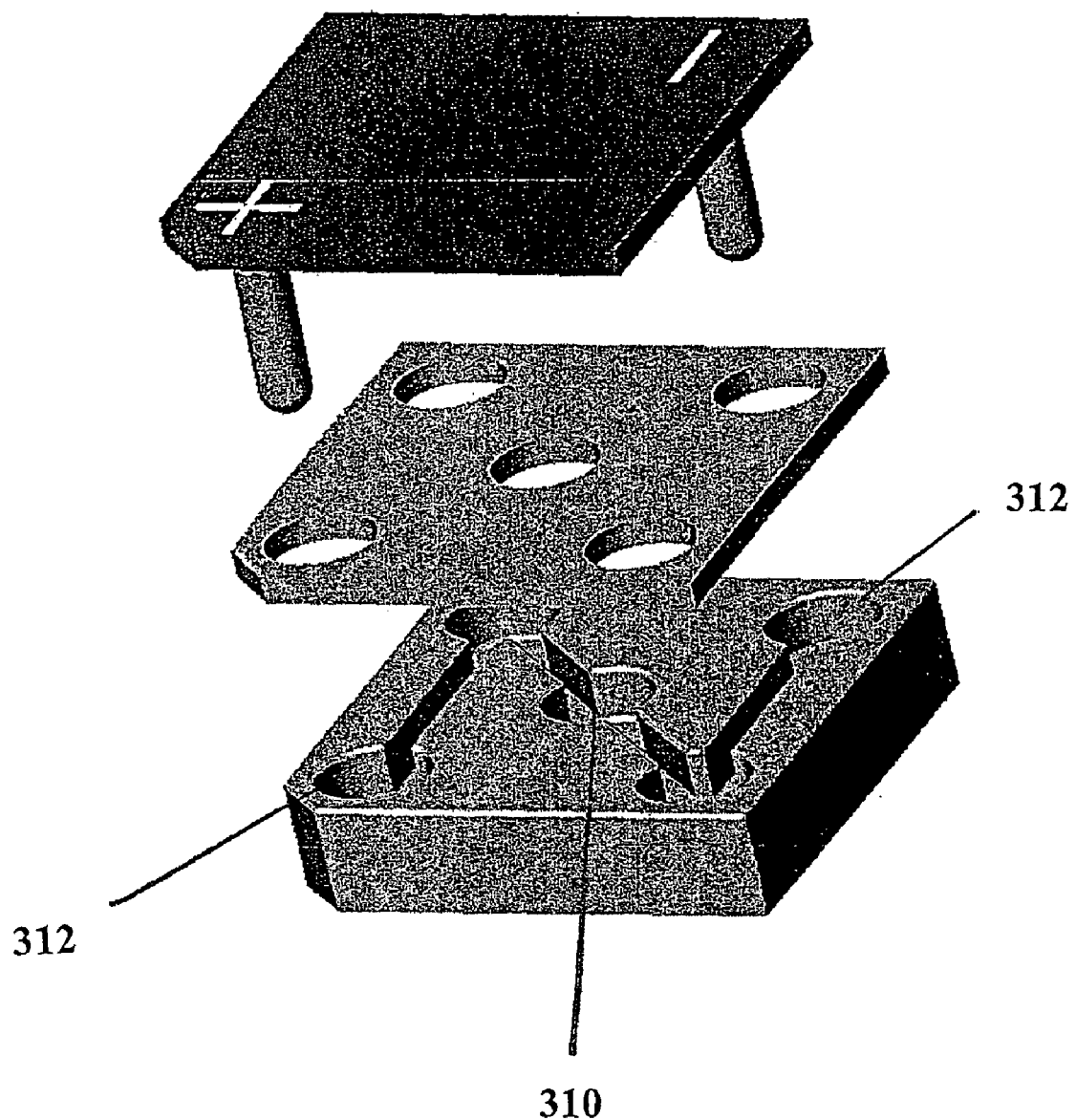
FIG. 3: A schematic for a "two-capture" format unit of the microstructure plate with electrode assembly with the sample accepting chamber (310) at the center of the N and electrode chambers (312) at the ends of the N.
Figure 8A:
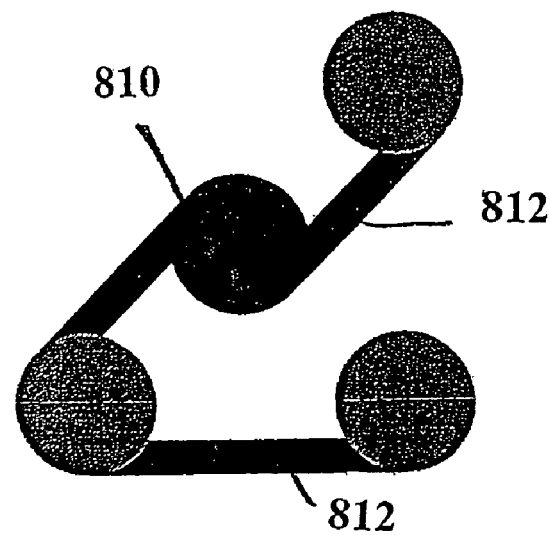
FIGS. 8a & b: Schematics of alternative microstructure section/chamber (810) and channel geometries (812). 8a shows an alternative channel arrangement. This geometry forces the molecules to enter the capture chamber from one end and exit from the other end. This could also improve the electric field and separation of the charged molecules. 8b shows a variation with a rectangular-shaped capture chamber (820) orthogonal to the main channel (822), instead of the round chamber used in previous example devices. This geometry may provide a more uniform capture of the phosphorylated peptide on the cross. The fabrication of this structure in PDMS is similar to example 1; however, instead of a round membrane disc, a rectangular-shaped membrane would be inserted in the slot. Similar to other examples, 384 or 1536 of these structures could easily be created using polymer molding techniques in an 8.5X11 cm footprint.

Exemplary suitable microstructure units in planar formats are shown in FIGS. 2 and 3. FIG. 2 shows a one-capture format microstructure unit, which generally describes a V shape: with the sample accepting microstructure section, or chamber, is at the point of the V; the first and second electrodes microstructure sections are at the two tips of the V; and the capture microstructure section is between the sample accepting chamber and an electrode. An alternative embodiment is illustrated in FIG. 3, in which an N shaped structure houses two capture microstructure sections, each between the sample accepting chamber (in the center of the N) and an electrode chamber (at the ends of the N). Alternative geometries may be devised which use linear or sinuous paths. Another modification which may be used is an off-center placement of the channels connecting the microstructure sections, as shown in FIG. 8a. This arrangement may improve the electric field shape and the flow of the charged molecule of interest through or over the capture matrix.

Figure 8B:
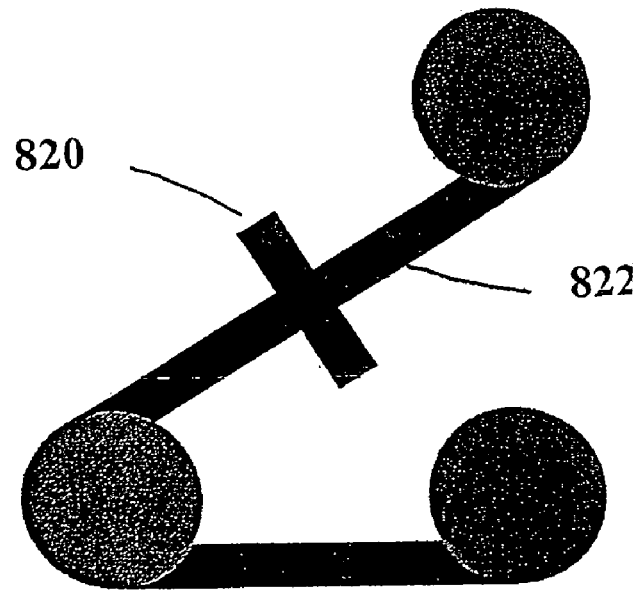
Figure 11:
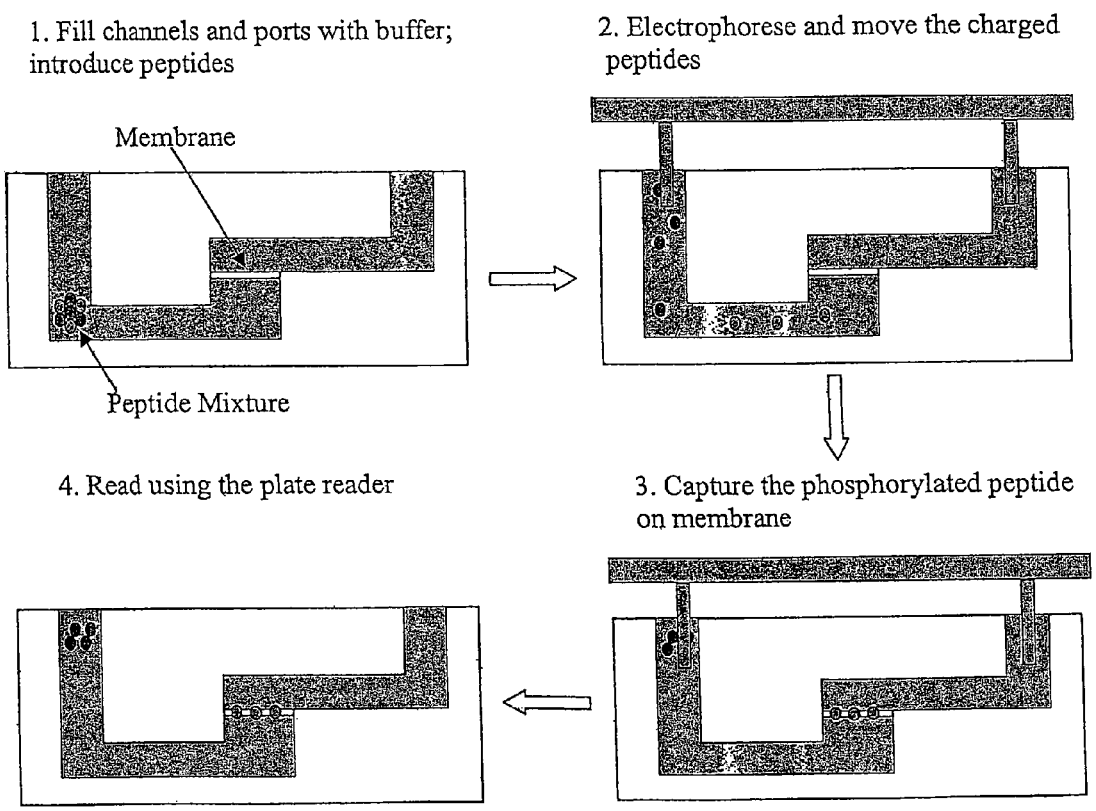
FIG. 11: An illustration of a three dimensional device of the invention being used for the separation of charged peptides.

As shown in FIG. 8b, which demonstrates a smaller rectangular capture section, forms other than round chambers may be used for the microstructure sections in the microstructures of the device. In fact, a constant width channel could be used, with the microstructure sections defined by ports for access (electrode and sample accepting sections), and the presence of the capture matrix in the capture microstructure section. Although it is preferred to keep the sample and electrodes separated in order to prevent electrochemical degradation of the sample, the sample accepting microstructure section and an electrode microstructure section may be the same, with the electrode being placed and the sample injected through the same opening in the microstructure plate (as shown in FIG. 11.)

Figure 9:
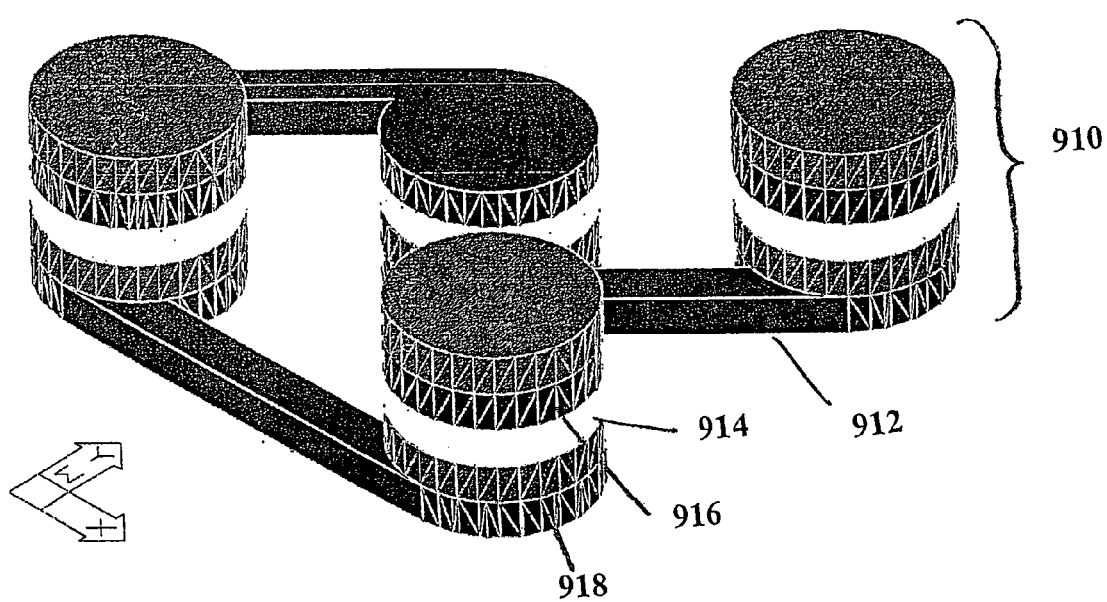
FIG. 9: A schematic of the system of chambers (910) and channels (912) created by the three dimensional embodiments of the present invention. Note that the capture matrix (914) is held between the third (916) and second (918) (from the bottom) layers of the center capture chamber.

In addition, the laminar structure of the microstructure plate may form a three dimensional structure, in which the microstructure sections and channels are not arranged in a coplanar format. An example of a three dimensional microstructure is shown in FIG. 9. An advantage to using these multi-layer structures is that a path for electrophoretic migration of the charged molecule of interest which is orthogonal to the capture matrix may be more easily produced in these microstructures, as the capture matrix may be held between the layers. Although the examples show arrays of single microstructures, embodiments in which two or more microstructure formats are arrayed on the same plate are also contemplated within the scope of the present invention.

The microchannels used to connect the microstructure sections are preferably of a size which minimizes electro-osmotic flow. In preferred embodiments, the microchannels between the microstructure sections of the microstructure have a cross-sectional area between 10,000 and 9,000,000 $\mu m^2$, more preferably between 10,000 and 250,000 $\mu m^2$, and most preferably between 25,000 and 250,000 $\mu m^2$. It is also preferred that the microstructure plate be made from a non-charged material in order to minimize electro-osmotic flow. Alternatively, the microstructure channels may be chemically modified to accomplish the same effect.

The microstructure plate is preferably comprised of a plastic polymer material such as polymethyl methacrylate (PMMA), polydimethylsiloxane (PDMS), or any other suitable polymer or combination of polymers. Additionally, materials such as silicon, glass, or coated metal may be used in constructing the microstructure plate. It is preferred that at least one layer of the microstructure plate be made from a transparent material in order to allow optical access to the microstructure and the capture matrix. The microstructures may be created in the microstructure plate layers by photolithographic techniques, injection molding, hot embossing techniques or other suitable methods. The microstructure plate comprises at least two layers: a sealing plate layer, which seals at least one channel or microstructure section, and at least one other layer of the microstructure which forms the microstructure sections and connecting channels. The sealing plate "seals" a microstructure section or channel by forming at least one side of the microstructure or channel and forming a liquid-tight seal with the other layers of the microstructure plate. In one preferred embodiment, the microstructure plate comprises a layer molded from a polymer material (usually by polymerizing over a master mold) and a sealing plate having openings (made by micro-machining or also by molding) that correspond to and align with the electrode and sample accepting microstructure sections of the first layer. Alternatively, the first layer may be molded with openings (e.g., by using a clamp molding technique), and the sealing plate may comprise a flat layer without any openings. This embodiment may be preferred when sample injection and/or access to the electrode assembly is to occur on one face of the microstructure plate, while detection is to occur on the other side of the microstructure plate.

The sealing plate may be comprised of a similar, or of a different material, as the first layer. The sealing plate interfaces with, and is preferably integral with, the first layer plate. This may be accomplished by using self-sealing materials for the plates, or by heat or adhesive bonding of the plates. Because PDMS will self-bond to other PDMS, glass, quartz, polystyrene, and other materials after oxygen plasma cleaning, PDMS is a preferred material for use as either the first layer or sealing plate.

Figure 7:
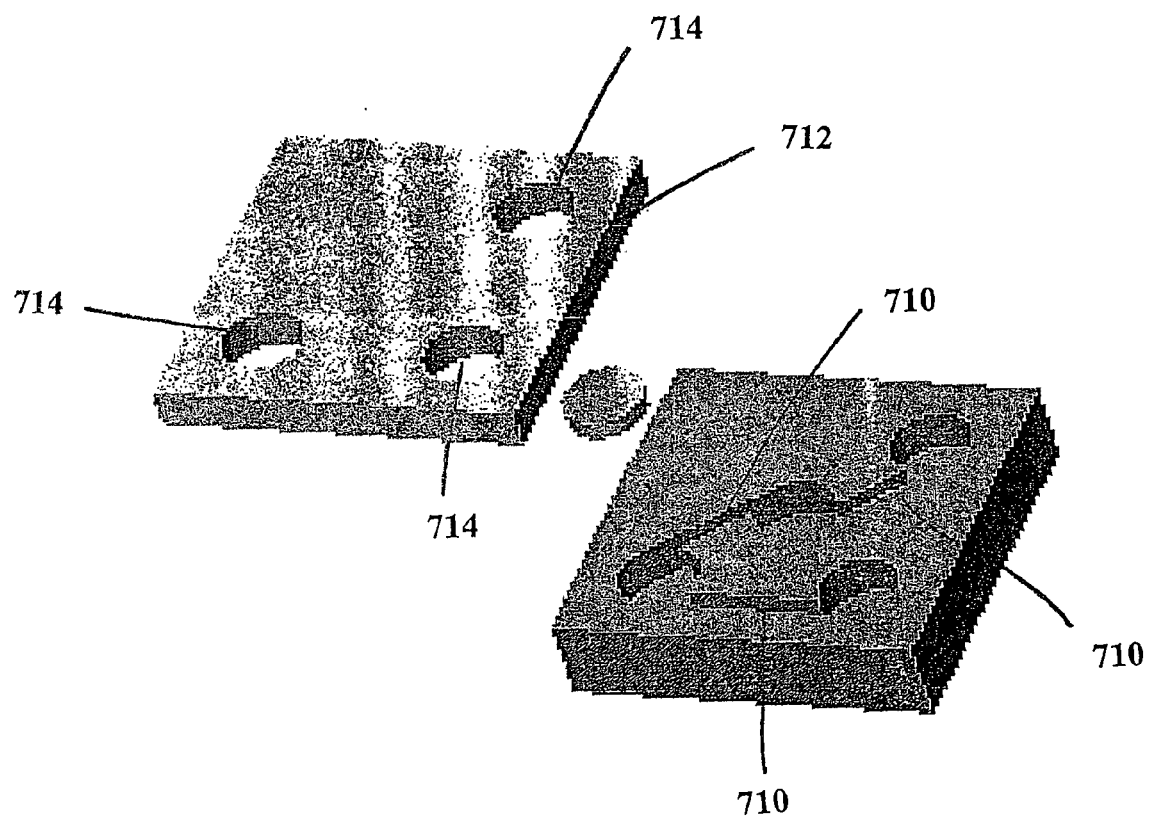
FIG. 7: A schematic of a two-layer microstructure plate device. Microchannels (710) and sections may be created in polymer layers by micromachining, laser ablation, injection molding, embossing, or other appropriate methods. A membrane disc can then be inserted in the capture section. The top polymer sealing-plate (712) may have openings for the introduction of samples and electrodes at the appropriate microstructure sections (714), as shown. 384 or 1536 of these microstructures would created in an 8.5X11 cm footprint. The device may then be used in methods similar to Example 2.
Figure 10:
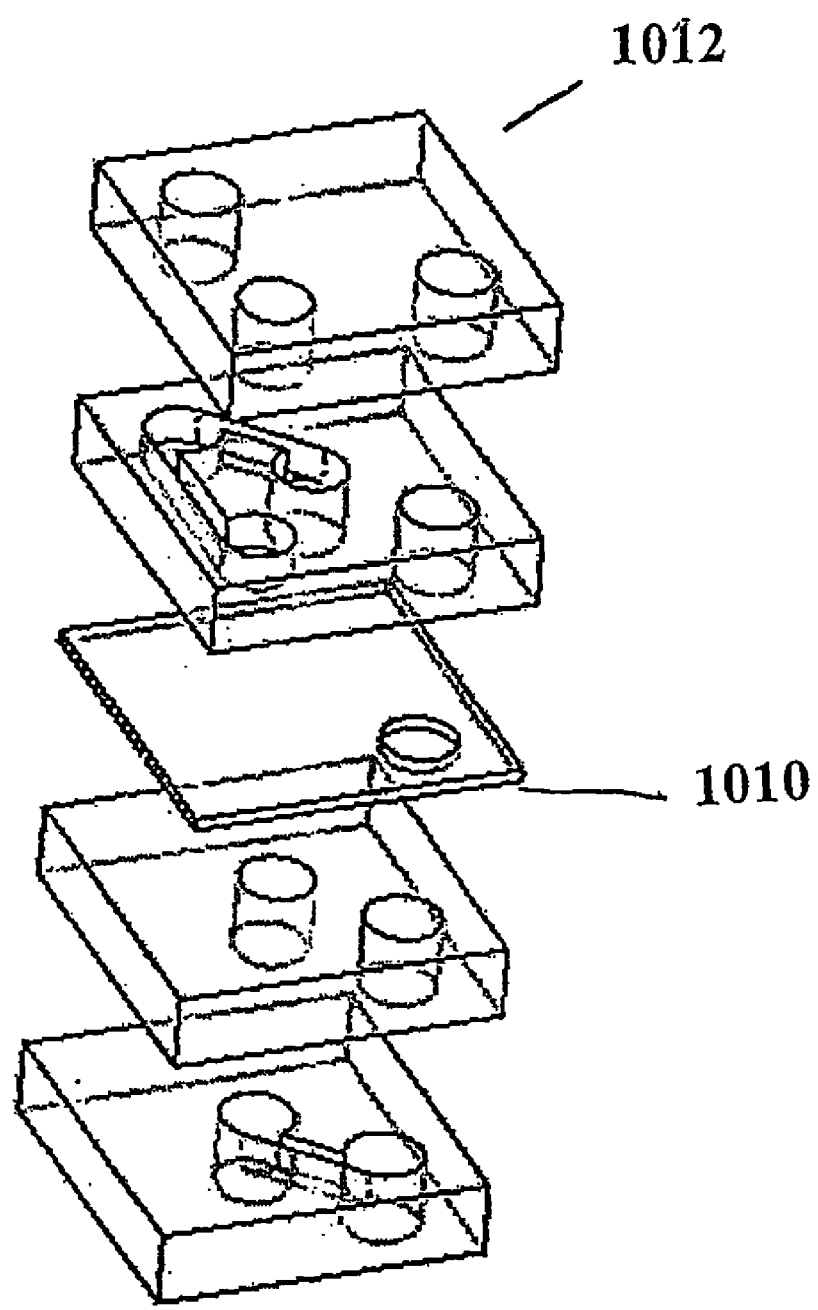
FIG. 10: A schematic of the construction of a three dimensional microstructure unit from inner polymer layers, a membrane layer (1010) (flat sheet) and outer polymer layers (1012) (top layer, pictured, and solid base layer, not pictured).

Multiple layers of PDMS or other materials may be used to form three dimensional structures. By layering several two-dimensional voids, a three dimensional channel structure such as depicted in FIG. 9 may be formed. As above, self-sealing materials such as PDMS are preferred for these structures, as they eliminate the need for heat-sealing or adhesive layers. Alternatively, the microstructures may be constructed by aligning a number of layers which have been machined or molded to form the microstructure sections and connecting channels. By utilizing this method of construction, three dimensional and planar structures may be easily made, as illustrated in FIGS. 7 and 10.

Capture Matrix Materials and Placement

The capture microstructure section includes a material that serves as a capture matrix to capture positively or negatively charged molecules. The capture matrix comprises a material having the ability to bind molecules of interest specifically or nonspecifically or to significantly retard their movement. The capture matrix may be comprised of, for example, a membrane disc cut to specification or a gel prepared in the capture microstructure section. If a binding, type capture matrix is utilized, the capture matrix may be placed within the microstructure so that the molecule of interest electrophoreses either tangential to (across) or orthogonal to (through) the surface of the capture matrix. The capture matrix may be placed within the capture microstructure section during the fabrication of the microstructure plate, or may be placed after the plate is assembled (e.g., by using a photomask to polymerize a hydrogel-forming monomer injected through an opening to the exterior of the microstructure plate). Capture matrix materials which bind the molecule of interests do so by chemically interacting with the charged molecule of interest through covalent bonding, hydrogen bonding, ionic bonding, Vander Waals interactions, or other molecular interactions.

Capture matrix materials which bind the molecule of interests do so by chemically interacting with the charged molecule of interest through covalent bonding, hydrogen bonding, ionic bonding, Van der Waals interactions, or other molecular interactions. Suitable capture matrix materials which may specifically bind to a molecule of interest include antibodies, streptavidin, avidin, and similar high-affinity binding materials. Alternatively, the capture matrix may combine a non-specific binding material such as metal chelate resins, anionic resins, cationic resins, polyvinylidine fluoride, nitrocellulose, or positively charged nylon. An example of a non-specific binding membrane is Biodyne B (available from Pall, Inc.), or other suitable membrane, which may be easily cut to the size of the capture microstructure section.

Alternately, the capture matrix may be comprised of a material that does not interact with the molecules of interest per se, but which significantly retards the molecule's electrophoretic transport so as to retain the molecule within the matrix for detection and quantification. These materials generally work on molecular sieving principles. Suitable movement-retarding materials include cellulose, glass fiber, nylon, and hydrogels. Preferred hydrogels for use in capture matrices include agarose, polyacrylamide, aminopropylmethacrylamide, 3-sulfopropyldimethyl-3-methacrylamidopropylammonium inner salt, methacrylic acid, 3-sulfopropylmethacrylate potassium salt, glycerylmonomethacrylate, and derivatives thereof. An example hydrogel for use is a solution of 10% acrylamide (19:1 acrylamide: bis-acrylamide), 0.5% Darocure 4265 (Ciba-Geigy) and 50 mM Tris-Cl, pH 8.0. The prepared monomer mixture may be pipetted into the capture microstructure section (or the entire microstructure if a photomask is used in the photo-curing step) and the microstructure plate UV-irradiated for 30 seconds in an UV curing light box to polymerize the acrylamide.

Electrode Assemblies

The electrode assembly comprises at least one cathode and at least one anode, which may be shared between one or more microstructures, or which may be for a single microstructure unit. In a preferred embodiment, the electrode assembly comprises an array of paired pin first and second electrodes fixedly attached to a rigid support, so that a pair of pin electrodes may align with access openings for the first and second electrode microstructure sections, and electrically contact the microstructure sections when the system is assembled (as in FIGS. 2 and 3). The paired electrodes may be controlled individually or in tandem, and are electrically connected to a controlled power source (e.g., constant current or voltage). For example, the electrode assembly may comprise a rigid planar support including 768 pin electrodes, where an anode and a cathode pair correspond to each of 384 microstructures to address selected microstructure sections with DC current. Similarly, arrays of 192 or 3072 electrodes may be used for 96 unit and 1536unit devices, respectively.

The electrodes may be wires, strips, or other convenient shapes, and may be soldered, deposited, etched, or glued in place with epoxy. Electrodes may be made of any suitable conductive material, including platinum and platinum plated titanium, gold, carbon fibers, and conductive polymers. Although non-corroding materials are preferred for use in reusable embodiments of the invention, reactive metals such as aluminum, copper, or steel may be used in limited-use devices. The electrical contact may be direct, or may occur through a conducting medium (e.g., a glass capillary filled with a conductive-buffer-containing hydrogel).

Alternatively, the electrodes may be printed inside the planar member, and maintain electrical contact with the electrode microstructure section portion of the microstructures through openings in the bottom of the structure (i.e., an upside-down version of FIG. 2 or 3). For example, the electrodes may be strip metal electrodes formed in a stamping process or chemical etching process. Or, in wholly disposable multiple- or single-use devices, the electrodes may be integrally formed with the microstructure plate (e.g., by placing the electrodes within the layers of the microstructure plate before polymerization or molding, between two layers of the microstructure plate before sealing, or printing or otherwise depositing metal for the electrodes on the sealing plate).

Methods of Using the Systems of the Invention to Separate Differently Charged Molecules In general, the methods of the present invention comprise filling the microstructure with an electrophoresis liquid; introducing a sample into a sample accepting microstructure section of the apparatus; energizing the electrode assembly for a sufficient period of time to allow a charged molecule of interest in the sample to migrate towards an electrode of the electrode assembly and to be caught in the capture matrix; and detecting the charged molecule of interest caught in the capture matrix.

In preferred embodiments of the methods of the invention, an aqueous buffer is utilized as the liquid in the device. Suitable buffers for use in the electrophoretic methods of the invention include Tris hydrochloride buffers, Tris borate buffers, histidine buffer, β-alanine buffers, adipic dihydrazide buffers, and HEPES buffers. Alternatively, an organic or other non-buffering liquid, such as DMSO, may be used. When the systems and method of the invention are used to analyze the action of an enzyme upon a labeled substrate (e.g., kinase, phosphatase, or protease reaction assays), the enzyme buffer may be used. This has the advantage of allowing one to carry out the reaction in the sample accepting microstructure section of the system and immediately electrophoresing the products.

In preferred methods, the buffer and the sample are introduced to ensure proper filling of the microstructures. This may be performed by using pressure to pipette or by appropriate surface treatment of the channels and sections to aid in capillary flow. Filling may be done utilizing automatic pipettors designed for use with microtiter plates, or other sample handling equipment. For convenience, the system may be packaged pre-filled with an electrophoresis buffer, especially in instances where hydrogel capture matrices are used. It is important to avoid air bubbles in the microstructures of the device. An advantage of microstructure plates formed from transparent materials is that they allow visual inspection to ensure complete filling of the microstructures.

Optionally, the method may also include device assembly steps, such as the placement of the capture matrix within the microstructure plate, or aligning the electrode assembly with the microstructure plate and bringing it into electrical contact with the first and second electrode sections of the microstructures. These steps will depend on the particular structure of the system. After the sample has been injected into the sample accepting section of the microstructure, and the electrodes are in place, the electrodes are energized to create an electric field. The current, voltage and time depend upon such factors as capture matrix composition and buffer composition, and the total electromotive force necessary to move a particular charged substrate or product through the solution in a reasonable time frame. These factors are well known in the art, and persons skilled in the electrophoretic arts can ascertain, with a minimum of experimentation, the optimal voltage, amperage, and time to use with the devices of the invention in particular applications. In general, useful voltages range between 0.1V to 500V, more preferably between 0.5V to 100V, and most preferably 1V to 40V. Useful amperages range from 1 $\mu$A to 10 mA, preferably 3 $\mu$A to 5 mA, and most preferably 5 $\mu$A to 1 mA per microstructure.

Any suitable means for detection may be used in the methods of the invention, including consisting fluorometry, colorimetry, luminometry, mass spectrometry, electrochemical detection, and radioactivity detection. Fluorometry is preferred for use in the present invention, because of the ease handling fluorophores, and the commercial availability of fluorescent microtiter plate readers. Fluorescently labeled peptides for use in particular kinase, phosphatase, or protease reactions may be made by derivatization with a fluorescent moiety, as has been described in the relevant assay literature. An advantage of the systems and methods of the invention is that the electrophoretic process and the detection process may be separated in time. Where a binding capture matrix is utilized, the detection process may be carried out from several minutes up to one hour after electrophoresis. However, if a movement-retarding capture matrix is used, detection should take place promptly after electrophoresis in order to avoid diffusion of the charged molecule of interest.

In an illustrative method of using the system of the invention, each of the microstructures is first mostly filled (about 90–98%, depending on sample volume) with a buffer, such as 50 mM Tris HCl, via an opening to the sample accepting microstructure section. Preferably, an automated pipettor, such as a CyBi 384/1536 pipettor (CyBio) or Tango Systems (Robbins Scientific) is used to fill the microstructures. Each sample comprising molecules of different net charges, such as for example, a peptide containing positively and negatively charged fluorescent-labeled peptide is loaded into a sample accepting microstructure section. The electrode assembly is then lowered onto the interfacing microstructure plate so that the electrodes electrically contact the first and second electrode microstructure sections. Upon electrophoresis, the molecules are selectively transported and concentrated in the capture matrix by the electrophoretic force of the energized electrodes. Molecules having a negative charge move towards the anode and may be sequestered by the capture matrix, which is disposed in the capture microstructure section, as in FIGS. 2 and 4a. Preferably, the capture microstructure section is designed to map to the center of a microtiter plate well. Alternately, molecules having a positive charge move towards the cathode and become electrochemically reduced or sequestered by another capture matrix place between the sample and the cathode, as in FIG. 3. The electrode assembly may then be removed, and the microstructure plate may be placed in a commercial plate reader for detection or quantification of the molecules of interest. Optionally, the microstructure plate may be covered with an optical mask with openings aligned with the capture microstructure sections in order to facilitate reading the signal in each capture microstructure section while minimizing background signal from the neighboring microstructures.

Utilizing these methods, very good sensitivity has been obtained in detecting the enzymatic conversion of substrates (e.g., kinase or phosphatase phosphorylation/dephosphorylation, or protease reactions). The systems and methods of the invention are able to detect about 10%, more preferably about 1.0%, and most preferably about 0.1% conversion of a labeled substrate in enzymatic reactions. The high sensitivity and convenient format of these systems make them ideal for use in high-throughput drug screening applications.

Sample preferred electrophoresis systems and methods for separating charged molecules, and many of their attendant advantages, are described in the following examples. It will be apparent, however, that various changes may be made in the form, construction and arrangement of the components and the content and sequence of the steps without departing from the spirit and scope of the invention, the forms and methods described herein being merely preferred or exemplary embodiments thereof. Therefore, the invention is not to be restricted or limited except in accordance with the following claims and their legal equivalents.

EXAMPLES

Example 1

Electrophoretic Planar Microstructures Formed in PDMS

Figure 4B:
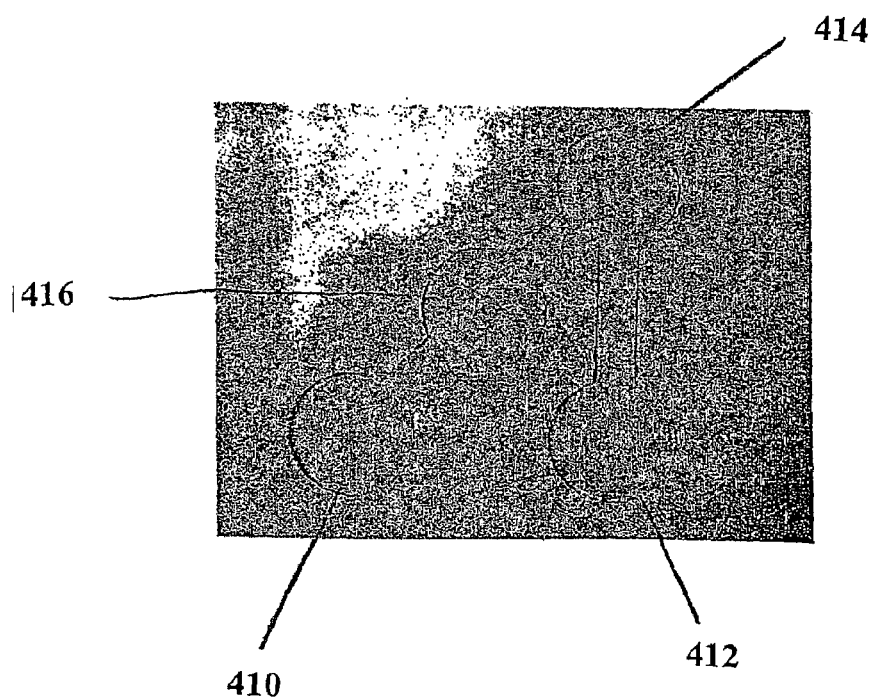
FIG. 4b: A photograph of the microstructure depicted in 4a, molded in polydimethylsiloxane from a master, fabricated from cured SU-8 photoresist on a silicon wafer illustrating the (+) electrode port (410), the (−) electrode port (412), the sample port (414), and the capture microstructure section (416).

Microfluidic structures were fabricated using SU-8 photoresist and poly(dimethylsiloxane) (PDMS). 384 single capture format microstructures with port size of 1 mm and channel size of 250 $\mu$m were designed in an 8.5X11 cm footprint similar to microtiter plates, as shown in FIG. 1. This design was converted into a transparency by a high-resolution printer. The transparency was used as a mask in photolithography to create a master in SU-8 photoresist. PDMS cast against the master yielded a polymeric replica containing 384 of the desired microstructures. The surface of this replica was then oxidized in oxygen plasma. Oxidation of the PDMS yields channels whose walls are negatively charged when in contact with neutral and basic aqueous solutions. These channels have the advantage of being filled easily, even with liquids with high surface energies (especially water). As shown in FIG. 4b, fairly clean channels and microstructure sections can be fabricated in PDMS.

Example 2

Use of the PDMS Planar Structures to Separate Kinase Products from Substrates Each microstructure used in these experiments was composed of 4 ports and three channels, as depicted in FIG. 4b.

In general, the sample (a peptide substrate mixture which has been reacted with a kinase enzyme) is introduced through an opening in the sealing plate into the sample chamber (S). The electrode assembly is then energized, biasing the (+) and (−) chambers positive and negative, respectively. Negatively charged components of the sample migrate toward the positive electrode and into the capture port (C). This port contains a matrix (Biodyne B, Pall Inc.) that irreversibly binds peptide and is located in the center of the structure to allow fluorescence detection with a standard plate reader.

Figure 5A:
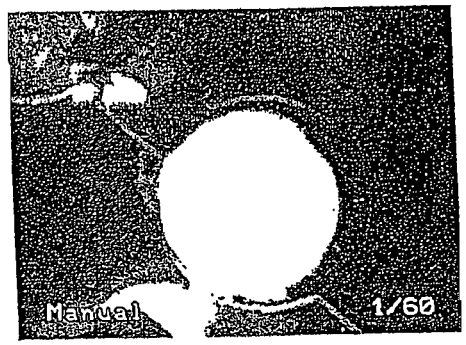
FIG. 5a: A white-light photograph of a portion of the micro structure pictured in FIG. 4b, assembled with a membrane capture matrix (white disc).
Figure 5B:
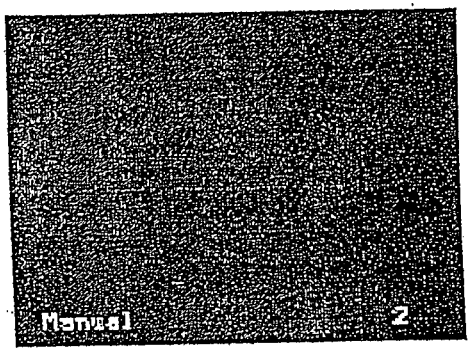
FIG. 5b: A fluorescence photograph of the result of the electrophoretic separation experiment in Example 2, when an unphosphorylated peptide is placed into the sample chamber.
Figure 5C:
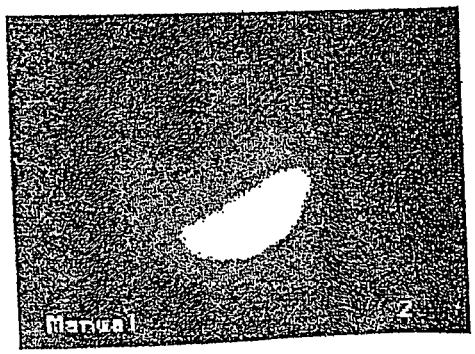
FIG. 5c: A fluorescence photograph of the result of the electrophoretic separation experiment in Example 2, when a phosphorylated peptide is placed into the sample chamber.
Figure 6:
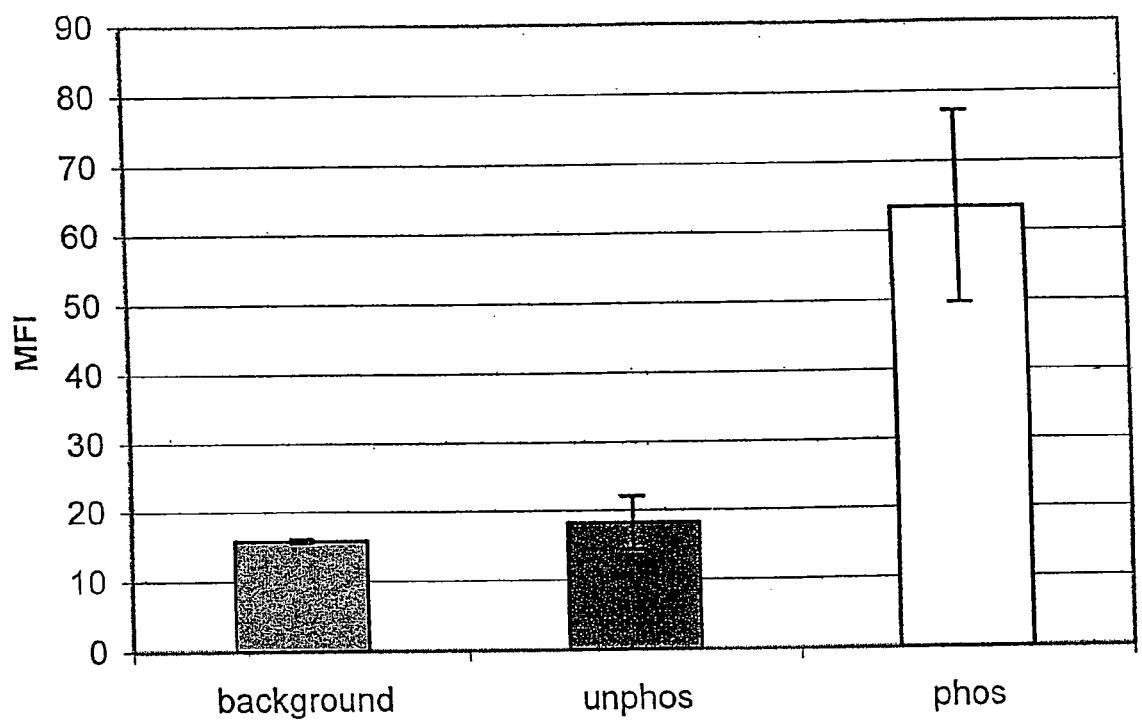
FIG. 6: A graphical representation of the data from FIGS. 5a–c.

Kemptide discrimination assays were performed in PDMS structures fabricated as described in Example 1. A 0.9 mm diameter Biodyne B membrane disc was inserted into the capture port. The structure was then filled with approximately 1.5 $\mu$l of 50 mM Tris-Cl pH 8.0. A sample pin was used to introduce 20 nl of 10 $\mu$M kemptide solution into the microstructure through an opening above the sample chamber. Platinum wire electrodes were placed in the electrode ports and a potential of 5V was applied. The resulting current ranged from 42 to 50 $\mu$A and steadily decreased. This experiment was repeated four times with both phosphorylated (kinase modified) and unphosphorylated peptides. FIGS. 5$a$–$c$ shows fluorescence (excitation: 594 nm, emission: 630 nm) at the capture port after 5 minutes of electrophoresis. Mean fluorescence intensity over the area of the capture port was quantified. The values demonstrate discrimination of phosphorylated from unphosphorylated kemptide, as shown in the graph in FIG. 6.

Example 3

3D Electrophoretic Microstructures

The microstructures described in example 1 could be modified to have several more layers, creating a three dimensional channel microstructure. When an electric field is applied across these structures, the molecules of interest may travel orthogonally through the capture matrix to bind, rather than travelling tangentially across the capture matrix. Tangential-flow arrangements generally produce moon-shaped deposits on the capture matrix, as shown in FIG. 5$c$. Using and orthogonal flow approach may increase the uniformity and reproducibility of the signal on the capture matrix. A depiction of a three-dimensional channel and chamber microstructure is shown in FIG. 9.

One approach to making three-dimensional layered structures is to use several layers of perforated and formed polymer material. As illustrated in FIG. 10, a bottom polymer layer may be used which has molded channels and microstructure sections forming a portion of the microstructure. Then layers of molded or cut polymer material with through holes for the microstructure sections and/or molded channels may be added, with a membrane capture matrix sandwiched between them. Finally, another polymer layer may be added for use as a sealing plate.

Such three-dimensional channels could be created in PDMS. Several layers with through holes and through channels are created. Fabrication of each layer is similar to Example 1. However, a clamping system is used to create through holes in several of the layers. Next, the layers are aligned and bonded upon contact after oxygen plasma cleaning. By utilizing this method, a structure such as that depicted in FIG. 9 may be built relatively easily. The top layer is molded with three through holes as the three openings. The next layer is molded with 4 holes and a channel. The next two layers sandwich the capture membrane, e.g. a sheet of Biodyne B membrane with crushed pores around the capture matrix chamber (to prevent side leakage) and through holes corresponding to the other chambers. The last layer would have two channels and four through holes. The sample (peptide mixture) would be introduced to the sample chamber and driven toward the capture chamber, down to the black channel below. This forces the molecule of interest (e.g. a charged peptide) to move orthogonally against the capture membrane.

We claim:

1. A system for separating molecules having different charges and capturing a molecule of interest for detection, comprising:
   a) a microstructure plate comprising:
      at least one microstructure, each microstructure comprising a series of microstructure sections and channels, wherein each microstructure section is directly interconnected to at least one other microstructure section by at least one channel, the series comprising:
      at least one sample accepting microstructure section for introducing sample into the microstructure plate, wherein the sample accepting microstructure section does not have an electrode and is fluidly connected to the exterior of the microstructure plate;
      at least one first electrode microstructure section;
      at least one second electrode microstructure section;
      at least one capture microstructure section containing a capture matrix, wherein the capture microstructure section is between the first and second electrode microstructure sections in the series;
      wherein the microstructures in the microstructure plate are formed by at least two layers of material, wherein at least one layer is a sealing plate layer which seals at least one channel or microstructure section in the microstructure plate; and
   b) an electrode assembly, the electrode assembly having at least one first and at least one second electrode, wherein each first electrode microstructure section is in electrical contact with at least one first electrode, and wherein each second electrode microstructure section is in electrical contact with at least one second electrode.

2. The system of claim 1 wherein the sealing plate comprises at least one opening to the exterior of the microstructure plate.

3. The system of claim 2 wherein at least one opening of the sealing plate aligns with at least one sample accepting microstructure section.

4. The system of claim 2 wherein at least one opening of the sealing plate aligns with at least one electrode microstructure section.

5. The system of claim 4 wherein each electrode of the electrode assembly extends through at least one opening in the sealing plate towards at least one electrode microstructure section.

6. The system of claim 2 wherein at least one opening of the sealing plate aligns with the capture microstructure section.

7. The system of claim 1 wherein at least one layer of the microstructure plate other than the sealing plate comprises at least one opening to the exterior of the microstructure plate.

8. The system of claim 7 wherein at least one opening of the non-sealing plate layer aligns with at least one sample accepting microstructure section.

9. The system of claim 7 wherein at least one opening of the non-sealing plate layer aligns with at least one electrode microstructure section.

10. The system of claim 9 wherein each electrode of the electrode assembly extends through at least one opening in the non-sealing plate layer towards at least one electrode microstructure section.

11. The system of claim 1 wherein the microstructure plate comprises two capture microstructure sections, wherein one capture microstructure section is positioned in the series between the sample accepting microstructure section and the first electrode microstructure section, and the second capture microstructure section is positioned in the series between the sample accepting microstructure section and the second electrode microstructure section.

12. The system of claim 1 wherein at least one layer of the microstructure plate is transparent to light.

13. The system of claim 1 wherein the capture matrix comprises a material having the ability to covalently or non-covalently bind at least one molecule of interest.

14. The system of claim 13 wherein the capture matrix is positioned within the capture microstructure section so that the molecule of interest travels across the microstructure tangential to the surface of the capture matrix when the first and second electrodes are energized to produce an electric field.

15. The system of claim 13 wherein the capture matrix is positioned within the capture microstructure section so that the molecule of interest travels through the microstructure orthogonal to the surface of the capture matrix when the first and second electrodes are energized to produce an electric field.

16. The system of claim 13 wherein the capture matrix binds the molecule of interest specifically.

17. The system of claim 16, wherein the capture matrix comprises an affinity binding material selected from the group consisting of antibodies, streptavidin and avidin.

18. The system of claim 13, wherein the capture matrix binds the molecule of interest non-specifically.

19. The system plate of claim 18 wherein the capture matrix comprises a material selected from the group consisting of metal chelate resins, anionic resins, cationic resins, polyvinylidine fluoride, nitrocellulose and charged nylon.

20. The system of claim 1 wherein the capture matrix impedes the movement of a molecule of interest.

21. The system of claim 20 wherein the capture matrix comprises a material selected from the group consisting of cellulose, glass fiber, nylon, and hydrogels.

22. The system of claim 21 wherein the capture matrix is a hydrogel selected from the group consisting of agarose, polyacrylamide, aminopropylmethacrylamide, 3-sulfopropyldimethyl-3-methacrylamidopropylammonium inner salt, methacrylic acid, 3-sulfopropylmethacrylate potassium salt, glycerylmonomethacrylate, and derivatives thereof.

23. The system of claim 20 wherein the capture matrix is positioned within the capture microstructure section so that the molecule of interest travels through the microstructure orthogonal to the surface of the capture matrix when the first and second electrodes are energized to produce an electric field.

24. The system of claim 1 wherein at least two channels connecting at least three microstructure sections lie in a three-dimensional configuration.

25. The system of claim 1 wherein the channels connecting the microstructure sections lie in a substantially planar configuration.

26. The system of claim 1 wherein the microstructure plate is comprised of more than two layers of material, the layers comprising a plurality of voids which define the microstructure sections and channels when the layers are aligned.

27. The system of claim 26 wherein the voids defining the channels of the microstructure lie within a single layer.

28. The system of claim 26 wherein the voids defining the channels of the microstructure lie within more than one layer.

29. The system of claim 26 wherein the capture matrix is held between two layers in order to position it within the capture microstructure section.

30. The system plate of claim 26 wherein at least one layer is formed from a self-sealing material.

31. The system of claim 30 wherein at least one layer is formed from a self-sealing material.

32. The system plate of claim 26, wherein at least one layer is formed from polytetrafluoroethylene.

33. The system of claim 1 wherein the channels between the microstructure sections of the microstructure have a cross-sectional area between 10,000 and 9,000,000 $\mu m^2$.

34. The system of claim 1 wherein the channels between the microstructure sections of the microstructure have a cross-sectional area between 10,000 and 250,000 $\mu m$.

35. The system of claim 1 wherein the channels between the microstructure sections of the microstructure have a cross-sectional area between 25,000 and 250,000 $\mu m_2$.

36. The system of claim 1 wherein the microstructure plate is approximately 8.5 cm. by 11 cm.

37. The system of claim 36 wherein the microstructure plate comprises a plurality of rectangularly arrayed microstructures.

38. The system of claim 37 wherein the microstructure plate comprises 96 rectangularly arrayed microstructures.

39. The system of claim 37 wherein the microstructure plate comprises 384 rectangularly arrayed microstructures.

40. The system of claim 37 wherein the microstructure plate comprises 1536 rectangularly arrayed microstructures.

41. The system of claim 37 wherein the electrode assembly comprises 192 regularly arrayed sets of first and second electrodes.

42. The system of claim 37 wherein the electrode assembly comprises 768 regularly arrayed sets of first and second electrodes.

43. The system of claim 37 wherein the electrode assembly comprises 3072 regularly arrayed sets of first and second electrodes.

44. The system of claim 1 wherein the electrode assembly is integrated within the material of the microstructure plate.

45. The system of claim 44 wherein the electrode assembly is embedded within the sealing plate.

46. The system of claim 44 wherein the electrode assembly is a printed circuit on the sealing plate.

47. The system of claim 44 wherein the electrode assembly is held between two layers of the microstructure plate.

48. The system of claim 1 wherein the electrode assembly comprises an electrode support plate formed from a rigid or semi-rigid material, the electrodes being fixedly held on or within the electrode support plate.

49. The system of claim 1 wherein each pair of first and second electrodes in the electrode assembly is controlled individually.

50. The system of claim 1 wherein all first electrodes in the electrode assembly and all second electrodes in the electrode assembly are controlled together.

* * * * *